United States Patent [19]

Crabtree et al.

[11] 3,957,437

[45] May 18, 1976

[54] METHOD FOR DETECTION OF GLYCOLATES

[75] Inventors: Eleanor V. Crabtree, Towson; Edward J. Poziomek, Bel Air, both of Md.

[73] Assignee: The United States of America as represented by the Secretary of the Army, Washington, D.C.

[22] Filed: May 17, 1974

[21] Appl. No.: 470,779

Related U.S. Application Data

[60] Division of Ser. No. 238,711, March 23, 1972, Pat. No. 3,903,080, which is a continuation of Ser. No. 854,811, Aug. 29, 1969, abandoned.

[52] U.S. Cl. .............................. 23/230 B; 23/230 R; 252/408
[51] Int. Cl.² ................. G01N 21/06; G01N 33/16
[58] Field of Search ...................... 23/230 R, 230 B; 252/408

[56] References Cited
OTHER PUBLICATIONS
John E. Spikner et al., Anal. Chem., 34, 1468–1471 (1962).

Primary Examiner—Morris O. Wolk
Assistant Examiner—Sidney Marantz
Attorney, Agent, or Firm—Nathan Edelberg; Robert P. Gibson; Robert W. Church

[57] ABSTRACT

Method and compounds for detecting glycolate incapacitating chemical agents; the detecting compounds have the generic formula

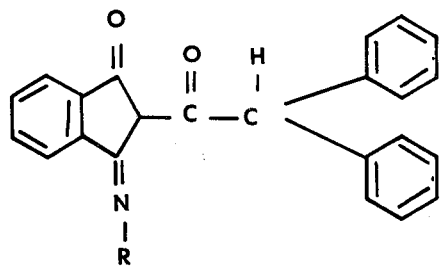

wherein R is an amino or imino group. The glycolate agents have the generic formula

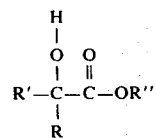

wherein R, R¹, and R¹¹ are each any aromatic group, any aliphatic group, any substituted aromatic group, any substituted aliphatic group, any cyclo aliphatic group, any cyclo aliphatic group having nitrogen in the cyclic structure, and any combinations thereof.

6 Claims, No Drawings

METHOD FOR DETECTION OF GLYCOLATES

DEDICATORY CLAUSE

The invention described herein may be manufactured, used, and licensed by or for the Government for governmental purposes without the payment to us of any royalty thereon.

This is a division of application Ser. No. 238,711 filed Mar. 23, 1972, now U.S. Pat. No. 3,903,080, which in turn was a continuation application of application Ser. No. 854,811 filed Aug. 29, 1969, now abandoned. This application also relates to applicants' application Ser. No. 230,541, filed Feb. 24, 1972, now abandoned, which in turn was a continuation of application Ser. No. 854,811 filed Aug. 29, 1969 and now abandoned.

Our invention relates to a composition of matter used to detect glycolate incapacitating chemical agents.

Since glycolate incapacitating agents act on the autonomic parasympathetic and central nervous systems, to interfere with transmission of impulses along a nerve or from nerve fibers to muscle fibers or secretory cells or from one nerve fiber to another across synapses in ganglia, and produce incapacitating physiological effects, a need exists to detect the presence of such glycolate agents in the atmosphere; such as could be encountered in field conditions during warfare. The prior art detection techniques of glycolates were based on chemical reactions, but, due to the lack of chemical reactivity of the glycolates, prior art chemical reaction techniques were not successful and did not solve the glycolate detection problem due to the complexity of the chemical reactions, lack of detection specificity, and lack of detection sensitivity. Our invention was conceived and reduced to practice to overcome the aforementioned prior art problems and to satisfy the long felt need for a relatively simple, easy to use, and sensitive means to detect glycolate agents with specificity.

A principal object of our invention is to provide, a means which will detect all glycolate incapacitating agents and which is a sensitive detection means.

Another object of our invention is to provide a means which will detect all glycolate incapacitating agents and which is relatively simple and easy to use to provide detection specificity.

Other objects of our invention will be obvious or will appear from the specification hereinafter set forth.

Our invention involves compositions of matter as glycolate chemical incapacitating agent detection means which are represented by the generic formula as follows:

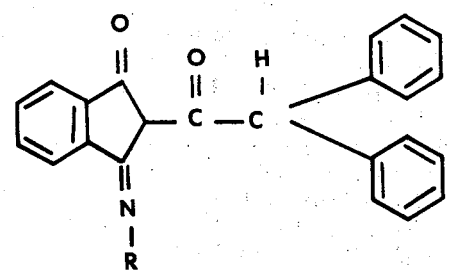

wherein R is any amino or imino group such as $NH_2$, $NHCH_3$, $NHCOC_6H_5$, $NHCOOC_2H_5$, $N=CHN(C_4H_9)_2$, $N=CHNHC_6H_5$, $N=CHNC_6H_5$, $N=C(OCH_3)(C_6H_5)$, $N=CHOC_4H_9$, $N=CHC_6H_5$, $N=C(CH_3)(C_6H_5)$, $N=C(OC_2H_5)(CHBr_2)$, $N=C(OC_2H_5)(CH_2Br)$, $N=C(CH_3)(CH_2NC_6H_5)Cl$, and $N(COC_6H_5)_2$. The compositions of matter of our invention are made by conventional methodology, such as disclosed in the publication TALANTA, 1968, Vol. 15, pages 482 to 484, Pergamon Press.

The glycolate agents which the above defined composition of matter will detect are represented by the generic formula as follows:

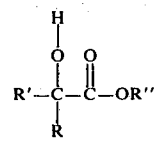

wherein R, $R^1$, and $R^{11}$ are any aromatic group, any aliphatic group, any substituted aromatic group, any substituted aliphatic group, any cyclo aliphatic group, and any cyclo aliphatic group having nitrogen in the cyclic structure. R, $R^1$, and $R^{11}$ can each be the same member of the aforementioned groups, or any combination of the aforementioned groups can be selected for R, $R^1$, and $R^{11}$.

The compositions of matter used as our detection means can all be prepared in the same manner as set forth in the exemplary procedures as follows.

EXAMPLE 1

A mixture of 1.75 grams of p-dimethylaminocinnamaldehyde and 2.92 grams of 2-diphenylacetyl-1, 3-indandione-1-hydrazone was stirred to produce a homogeneous mixture and refluxed in 50 ml of chloroform for 20 minutes; two drops of concentrated HCl being added to the reflux mixture prior to refluxing to act as a catalyst. A red solution was produced which was filtered hot to remove any unreacted starting materials. The filtered solution was cooled to room temperature and 100–200 ml of anhydrous ether was added which produced a red precipitate. The precipitate was removed from the solution through filtration and recrystallized from 50 ml of a boiling methanol-chloroform (10:1) mixture which yielded 4.61 grams of a brick red solid, 2-diphenylacetyl-1, 3-indandione-1-p-dimethylaminocinnamaldazine, having a melting point of 198°C.

Percent analysis for $C_{34}H_{29}N_3O_2$ Calcd: C, 79.8; H, 5.7; N, 8.2; O, 6.3 Found: C, 79.9; H, 5.7; N, 8.5; O, 6.2

EXAMPLE 2

A mixture of 2.50 grams of N-methiodide-4-pyridine carboxaldehyde and 2.92 grams of 2-diphenylacetyl-1, 3-indandione-1-hydrazone was stirred to produce a homogeneous mixture and refluxed in 50 ml of chloroform for thirty minutes; two drops of concentrated HCl being added to the reflux mixture, prior to refluxing, to act as a catalyst. The refluxed solution was cooled to room temperature, and a brownish orange product began to precipitate on cooling. After cooling to room temperature, 100–200 ml of anhydrous ether was added, and a brownish orange product precipitated. The product was extracted with 50 ml of a hot methanol-chloroform (10:1) mixture. After filtering the mixture while hot, 4.65 grams of a brownish orange solid, 2-diphenylacetyl-1, 3-indandione-1-p-N-methiodidepyridine carboxaldazine was obtained which had a melting point of 230°C.

Percent analysis for $C_{30}H_{20}IN_3O_2$ Calcd: C, 62.0; H, 3.5; I, 21.8; N, 7.5; O, 5.5 Found: C, 61.5; H, 4.3; I, 21.7; N, 7.1; O, 5.0

The efficacy of all of the compositions utilized in our technique were tested as shown in the following exemplary procedure.

EXAMPLE 3

10 milligrams of detection composition means of 2-diphenylacetyl-1, 3-indandione-1-p-N methiodidepyridine carboxyaldazine was dissolved in 10 milliliters of tetrahydrofuran acidified with 2-3 drops of concentrated HCl. Glycolate incapacitating chemical agent was spotted as an ethanolic solution on the grid side of a conventional Gelman glass microfiber sheet. The detection composition means was sprayed as a very fine mist onto the glycolate spotted grid side. Upon viewing the microfiber sheet, as soon as the solvent had volatilized (1-2 minutes), under either long or short wave ultra violet light, the long wave being generally more sensitive, yellow fluorescent spots were visible which demonstrated the presence of glycolate incapacitating agent. As a result of our testing, we determined that the presence of as little as 0.1 micrograms of glycolate incapacitating agent can be detected by our method. The detection composition can be sprayed by either a Freon propelled spray can or by air driven spray; both spray techniques being those as conventionally used in thin layer chromatography. In the case of the Freon spray can, a three ounce can was used which contained 20 grams of the detection composition of our invention, 40 grams of trichloromonofluoromethane, and 40 grams of dichlorodifluoromethane.

EXAMPLE 4

10 milligrams of detection composition means 2-diphenylacetyl-1, 3-indandione-1-p-dimethylaminocinnamaldazine was dissolved in 30 milliliters of glacial acetic acid to which 0.65 ml of concentrated HCl was added. Glycolate incapacitating chemical agent was spotted as an ethanolic solution on the grid side of a conventional Gelman glass microfiber sheet. The detection composition means was sprayed onto the glycolate spotted grid side as described in Example 3. The microfiber sheet was viewed with ultra violet light, as in Example 3, and a reddish-orange fluorescence was visible which demonstrated the presence of glycolate incapacitating agent.

Test results showed our glycolate agent detection technique to have an absolute sensitivity of $0.1\mu$, and temperature has little perceptible effect on the intensity of fluorescence in the range of −70°C to 100°C. Chromatographic and spectroscopic tests substantiated that the fluorescent emission in our technique is due to a weak association of molecules rather than a very fast chemical reaction.

While the glycolate incapacitating agent was sprayed on for test purposes, samples can be collected on any substrate and by any conventional sampling means to be tested by our technique and detection compositions for the presence of glycolate agent. Also, while we utilized acidified tetrahydrofuran and acetic/HCl acid as solvents, it is readily apparent that a variety of equivalent solvent systems based on other aqueous and/or organic solvents with suitable acids would be obvious to one of ordinary skill in the art.

We wish it to be understood that we do not desire to be limited to the exact details shown and described, for obvious modifications will occur to a person skilled in the art.

We claim:

1. A method for detecting the presence of glycolate compounds comprising:
    a. collecting a sample of a material suspected of containing a glycolate compound on a substrate,
    b. spraying onto the said sample on said substrate, a solution of a detecting compound having the generic structural formula wherein R is a member selected from the group consisting of amino and imino, said solution containing a solvent for said detecting compound,
    c. allowing said solvent to vaporize,
    d. viewing the substrate resulting from (c) in ultraviolet light; and
    e. concluding a positive test when a fluorescence in a color spectrum from yellow to reddish-orange is observed.

2. The method of claim 1 wherein R is a member selected from the group consisting of $NH_2$, $NHCH_3$, $NHCOC_6H_5$, $NHCOOC_2H_5$, $N = CHN(C_4H_9)2$, $N = CHNC_6H_5$, $N = CHNHC_6H5$, $N = C(OCH_3)(C_6H_5)$, $N = CHOC_4H_9$, $N = CHC_6H_5$, $N = C(CH_3)(C_6H_5)$, $N = C(OC_2H_5)(CHBr_2)$, $N = C(OC_2H_5)(CH_2Br)$, $N = C(CH_3)(CH_2NC_6H_5)Cl$, and $N(COC_6H_5)2$.

3. The method of claim 1 wherein the glycolate compounds being detected have the generic formula wherein R, $R^1$, and $R_{11}$ are members selected from the group consisting of aromatic, aliphatic, substituted aromatic, substituted aliphatic, cyclo aliphatic, cyclo aliphatic having nitrogen in the cyclic structure, and combinations thereof.

4. The method of claim 1 wherein a sensitivity of $0.1\mu$ is attained.

5. The method of claim 1 wherein the spraying is accomplished by a means selected from a Freon propelled spray can and an air driven spray.

6. The method of claim 5 wherein the contents of the Freon propelled spray can consists of 20 grams of detecting compound, 40 grams of trichloromonofluoromethane, and 40 grams of dichlorodifluoromethane.

* * * * *